(12) United States Patent
Handler

(10) Patent No.: US 9,528,945 B2
(45) Date of Patent: Dec. 27, 2016

(54) SYSTEMS AND METHODS FOR DETECTING CRACK GROWTH

(71) Applicant: The Boeing Company, Chicago, IL (US)

(72) Inventor: Jordan Jerome Handler, Seattle, WA (US)

(73) Assignee: The Boeing Company, Chicago, IL (US)

( * ) Notice: Subject to any disclaimer, the term of this patent is extended or adjusted under 35 U.S.C. 154(b) by 120 days.

(21) Appl. No.: 14/472,300

(22) Filed: Aug. 28, 2014

(65) Prior Publication Data

US 2016/0061748 A1    Mar. 3, 2016

(51) Int. Cl.
  *G01N 3/06* (2006.01)
  *G01N 21/95* (2006.01)
  *G01N 21/25* (2006.01)

(52) U.S. Cl.
  CPC .............. *G01N 21/95* (2013.01); *G01N 3/068* (2013.01); *G01N 21/255* (2013.01); *G01N 2203/0066* (2013.01); *G01N 2203/0652* (2013.01); *G01N 2203/0682* (2013.01)

(58) Field of Classification Search
  CPC .............................................. G01N 2203/0066
  See application file for complete search history.

(56) References Cited

U.S. PATENT DOCUMENTS

| | | | |
|---|---|---|---|
| 4,063,282 A * | 12/1977 | Exton | G01L 1/24 348/132 |
| 4,149,406 A | 4/1979 | Russenberger | |
| 4,519,041 A | 5/1985 | Fant et al. | |
| 4,574,642 A | 3/1986 | Fleischman | |
| 4,716,459 A | 12/1987 | Makabe et al. | |
| 5,291,279 A | 3/1994 | Imao | |
| 5,517,861 A | 5/1996 | Haas et al. | |
| 5,673,203 A | 9/1997 | Annigeri et al. | |
| 8,094,922 B2 * | 1/2012 | Lee | G01B 11/2518 382/141 |
| 2002/0139194 A1 * | 10/2002 | Mars | G01N 3/32 73/799 |

(Continued)

FOREIGN PATENT DOCUMENTS

GB        2108684 A        5/1983

OTHER PUBLICATIONS

ASTM International D 5045-99 (Reapproved 2007): Standard Test Methods for Plane-Strain Fracture Toughness and Strain Energy Release Rate of Plastic Materials, Jun. 2007, 9 pages.

(Continued)

*Primary Examiner* — Kara E Geisel
*Assistant Examiner* — Shawn Decenzo
(74) *Attorney, Agent, or Firm* — Kolisch Hartwell, P.C.

(57) ABSTRACT

A system and method for detecting crack propagation in a material test specimen may include color contrasting a surface of a test specimen, acquiring a plurality of photographic images of the specimen during application of a stress load, processing the plurality of images to detect characteristics of pixels that are outside a baseline range of pixel characteristics indicative of a contrast between a crack in the test specimen and the color contrasted surface of the test specimen, and generating an output of a strain energy release rate based on changes in detected crack length over time.

20 Claims, 6 Drawing Sheets

(56) References Cited

U.S. PATENT DOCUMENTS

| | | |
|---|---|---|
| 2009/0303469 A1 | 12/2009 | Lee et al. |
| 2010/0243387 A1 | 9/2010 | Vollert et al. |
| 2013/0044936 A1* | 2/2013 | Wang .................... G06T 7/0004 |
| | | 382/141 |
| 2013/0135460 A1* | 5/2013 | Syassen .................... G01L 1/00 |
| | | 348/129 |

OTHER PUBLICATIONS

European Patent Office, Extended European Search Report in European Patent Application No. 15176282.0, mnailed Jan. 29, 2016, 9 pages.

* cited by examiner

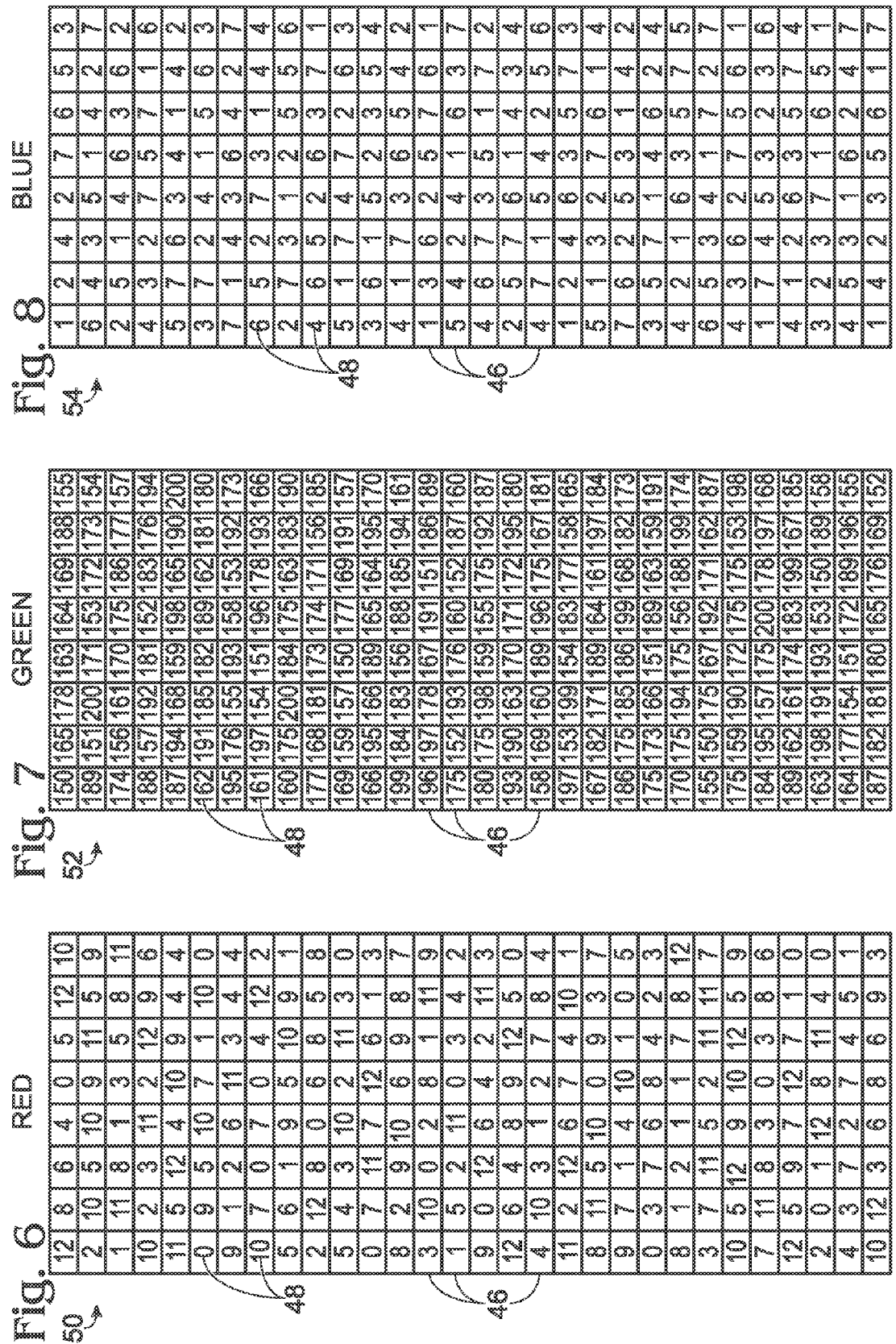

Fig. 9, Fig. 10, Fig. 11 — Pixel value tables for RED, GREEN, and BLUE color channels (reference numerals 56, 58, 60; with callouts 62 and 64).

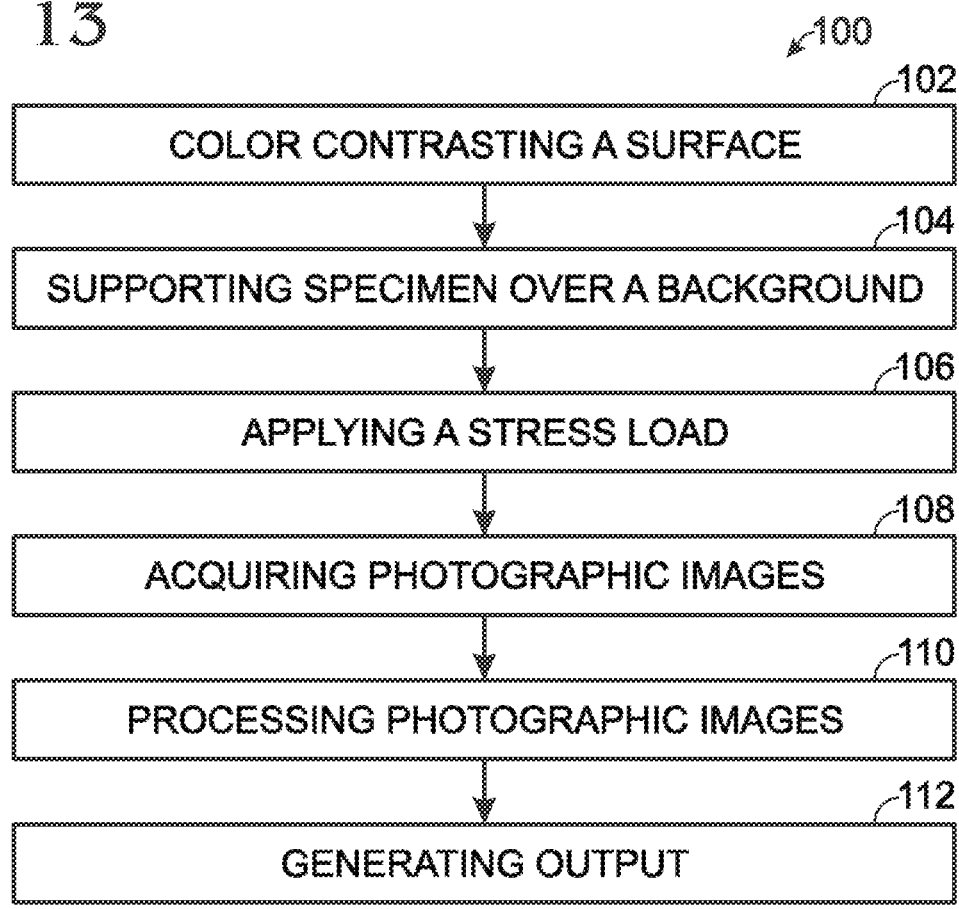

SYSTEMS AND METHODS FOR DETECTING CRACK GROWTH

CROSS-REFERENCES

The following related applications and materials are incorporated herein, in their entireties, for all purposes: U.S. Pat. Nos. 8,094,922; 5,673,203; 5,517,861; 4,716,459; 4,574,642; 4,519,041; and 4,149,406; and ASTM International D 5045-99 (Reapproved 2007): *Standard Test Methods for Plane-Strain Fracture Toughness and Strain Energy Release Rate of Plastic Materials*, June 2007, 9 pages.

FIELD

This disclosure relates to specimen testing. More specifically, the disclosed embodiments relate to systems and methods for detecting crack growth in a test specimen during application of a stress load.

BACKGROUND

Structural components and/or other materials may be tested to determine their material characteristics. Determining the material characteristics of a structural component and/or material may be important in determining, for example, whether or not that component or material is suitable for a particular use. In some tests, a specimen that is representative of a particular structural component and/or material may be selected. During the test, one or more forces may be applied to the test specimen to determine the characteristics of that specimen. In some tests, one or more forces may be applied to induce and/or propagate a crack in the test specimen. In those tests, measuring the crack length and the associated load provides information regarding the material characteristics of the test specimen. An example of a material characteristic that may be calculated based on the crack length and associated load is the strain energy release rate.

X-ray imaging equipment has been used to detect and measure cracks in test specimens. The X-ray imaging equipment can capture and process a limited number of images over a particular time period, such as about one image over a three-second period. Additionally, the cracks shown on the X-ray images typically are manually measured by a person using a ruler or tape measure (either physical or digital). Material characteristics are then calculated based on the measured crack length.

However, material characteristics of a test specimen may not be accurately determined or calculated using the above method. For example, only a limited number of X-ray images may be obtained during propagation of a crack in a test specimen as compared to the speed of a digital camera. Additionally, the cracks in the X-ray images may not be accurately measured by a person using a ruler; because x-ray images consist of averaged frames, there may be no clear indication of where a crack ends. Inaccurate determination of material characteristics may lead to selection of a component or material that is not suitable for its intended use, which may lead to premature failure of that component or material while in service.

SUMMARY

The present disclosure provides a method of detecting crack propagation in a material test specimen. In some embodiments, the method may include color contrasting a surface of a test specimen and acquiring a plurality of photographic images of the specimen during application of a stress load. In some embodiments, the method may include processing the plurality of images to detect characteristics of pixels that are outside a baseline range of pixel characteristics indicative of a contrast between a crack in the test specimen and the color contrasted surface of the test specimen. In some embodiments, the method may include generating an output of a strain energy release rate based on changes in detected crack length over time.

The present disclosure provides a system for detecting crack propagation in a material test specimen. In some embodiments, the system may include a test platform configured to support a material test specimen on a background. The material test specimen may have a top surface color contrasting a surface color of the background. In some embodiments, the system may include a camera directed toward the test platform and configured to acquire a plurality of photographic images of a test specimen located on the platform during application of a stress load to the test specimen. In some embodiments, the system may include an image processing program that receives the plurality of photographic images. The image processing program may be configured to detect, in the plurality of photographic images, pixel characteristics that are outside a baseline range of pixel characteristics, and measure changes in a detected crack length based on the detected pixel characteristics.

The present disclosure provides a method of detecting crack propagation in a material test specimen. In some embodiments, the method may include supporting a material test specimen over a background. The specimen may have a top surface color contrasting a surface color of the background. In some embodiments, the method may include applying a stress load to the specimen and acquiring multiple photographic images of an extending crack length in the specimen during the applying step. In some embodiments, the method may include detecting pixel characteristics that are different from pixel characteristics associated with the top surface color to measure crack length in the specimen.

The features, functions, and advantages may be achieved independently in various embodiments of the present disclosure, or may be combined in yet other embodiments, further details of which can be seen with reference to the following description and drawings.

BRIEF DESCRIPTION OF THE DRAWINGS

FIG. 6 is a schematic diagram of pixels of an illustrative photographic image of the test specimen of FIG. 2 showing illustrative red values for those pixels.

FIG. 7 is a schematic diagram of pixels of an illustrative photographic image of the test specimen of FIG. 2 showing illustrative green values for those pixels.

FIG. 8 is a schematic diagram of pixels of an illustrative photographic image of the test specimen of FIG. 2 showing illustrative blue values for those pixels.

FIG. 9 is a schematic diagram of pixels of an illustrative photographic image of the test specimen of FIG. 4 showing illustrative red values for those pixels.

FIG. 10 is a schematic diagram of pixels of an illustrative photographic image of the test specimen of FIG. 4 showing illustrative green values for those pixels.

FIG. 11 is a schematic diagram of pixels of an illustrative photographic image of the test specimen of FIG. 4 showing illustrative blue values for those pixels.

FIG. 13 is a flowchart depicting an illustrative method of crack growth detection.

DESCRIPTION

Overview

Figure 1:
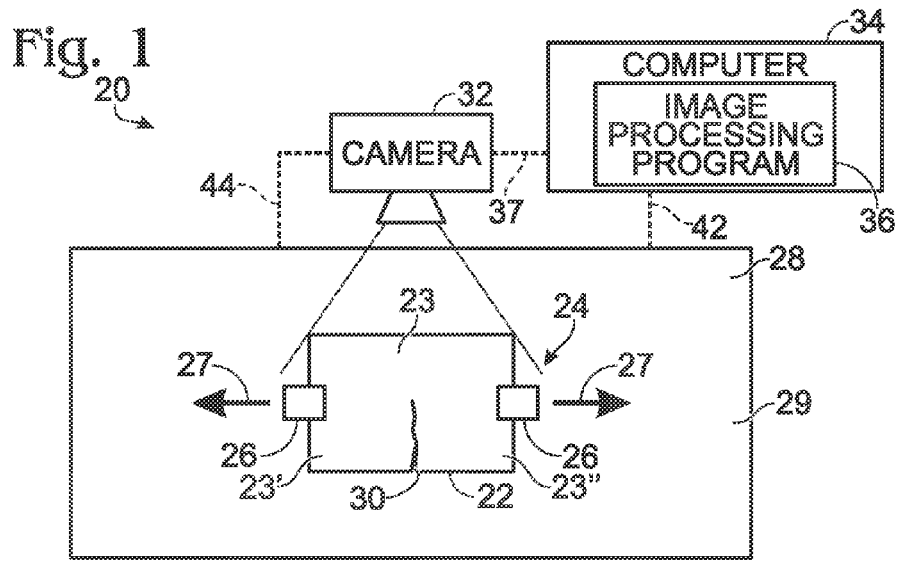
FIG. 1 is a schematic diagram of an illustrative crack detection system.

Various embodiments of systems and methods for detecting crack growth are described below and illustrated in the associated drawings. Unless otherwise specified, a system or method and/or its various components may, but are not required to, contain at least one of the structure, components, functionality, and/or variations described, illustrated, and/or incorporated herein. Furthermore, the structures, components, functionalities, and/or variations described, illustrated, and/or incorporated herein in connection with the present teachings may, but are not required to, be included in other similar systems and methods. The following description of various embodiments is merely exemplary in nature and is in no way intended to limit the disclosure, its application, or uses. Additionally, the advantages provided by the embodiments, as described below, are illustrative in nature and not all embodiments provide the same advantages or the same degree of advantages.

Aspects of the systems and methods for detecting crack growth may be embodied as a computer method, computer system, or computer program product. Accordingly, those aspects may take the form of an entirely hardware embodiment, an entirely software embodiment (including firmware, resident software, micro-code, and the like), or an embodiment combining software and hardware aspects, all of which may generally be referred to herein as a "circuit," "module," or "system." Furthermore, aspects of the systems and methods for detecting crack growth may take the form of a computer program product embodied in a computer-readable medium (or media) having computer readable program code/instructions embodied thereon, such as instructions to process a plurality of photographic images to detect characteristics of pixels (as further discussed below).

Any combination of computer-readable media for the systems and methods for detecting crack growth may be utilized. Computer-readable media can be a computer-readable signal medium and/or a computer-readable storage medium. A computer-readable storage medium may include an electronic, magnetic, optical, electromagnetic, infrared, and/or semiconductor system, apparatus, or device, or any suitable combination of these. More specific examples of a computer-readable storage medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, and/or any suitable combination of these and/or the like. In the context of this disclosure, a computer-readable storage medium may include any suitable tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electromagnetic, optical, and/or any suitable combination thereof. A computer-readable signal medium may include any computer-readable medium that is not a computer-readable storage medium and that is capable of communicating, propagating, or transporting a program for use by or in connection with an instruction execution system, apparatus, or device, such as the system for detecting crack growth of the present disclosure.

Program code for detecting crack growth embodied on a computer-readable medium may be transmitted using any appropriate medium, including but not limited to wireless, wireline, optical fiber cable, RF, and/or the like, and/or any suitable combination of these.

Computer program code for detecting crack growth may be written in one or any combination of programming languages, including an object-oriented programming language such as Java, Smalltalk, C++, and/or the like, and conventional procedural programming languages, such as the C programming language. The program code may execute entirely on a user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), and/or the connection may be made to an external computer (for example, through the Internet using an Internet Service Provider).

Aspects of systems and methods for detecting crack growth are described below with reference to flowchart illustrations and/or block diagrams of methods, apparatuses, systems, and/or computer program products according to aspects of the present disclosure. Each block and/or combination of blocks in a flowchart and/or block diagram may be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks, such as processing photographic images and generating output from that processing.

The computer program instructions for detecting crack growth can also be stored in a computer-readable medium that can direct a computer, other programmable data processing apparatus, and/or other device to function in a particular manner, such that the instructions stored in the computer-readable medium produce an article of manufacture including instructions which implement the function/act specified in the flowchart and/or block diagram block or blocks.

The computer program instructions for detecting crack growth can also be loaded onto a computer, other programmable data processing apparatus, and/or other device to cause a series of operational steps to be performed on the device to produce a computer-implemented process such that the instructions which execute on the computer or other programmable apparatus provide processes for implementing the functions/acts specified in the flowchart and/or block diagram block or blocks, such as processing photographic images and generating output from that processing.

Any flowchart and/or block diagram in the drawings is intended to illustrate the architecture, functionality, and/or operation of possible implementations of systems, and methods for detecting crack growth. In this regard, each block may represent a module, segment, or portion of code, which comprises one or more executable instructions for implementing the specified logical function(s). In some implementations, the functions noted in the block may occur out of the order noted in the drawings. For example, two blocks shown in succession may, in fact, be executed substantially concurrently, or the blocks may sometimes be executed in the reverse order, depending upon the functionality involved. Each block and/or combination of blocks may be implemented by special purpose hardware-based systems (or combinations of special purpose hardware and computer instructions) that perform the specified functions or acts for detecting crack growth.

Definitions

"Color contrast" refers to a surface of a test specimen that has a color that is different from the color of the interior of that specimen and/or from the color of a background. For example, the test specimen may be provided with a color contrasted top surface or layer. Alternatively, or additionally, a color contrast may be applied to the surface of the test specimen, such as a color contrast coating.

"Highly contrasted" refers to a surface of a test specimen that has a color with a mean and standard deviation for each of Red, Blue, and Green intensities such that each pixel of the background or sub-material (interior of specimen) contains at least one RGB component with a value outside the surface's mean value±three standard deviations.

"Pixel characteristics" refers to intensity, hue, lumosity, and/or saturation of the pixel.

"Pixel intensity" refers to the shade or level of the pixel that varies based on the color depth or the number of bits. For examples, the intensity values range from 0-255 for 24-bit ("true color").

"Strain energy release rate" is the energy dissipated during fracture per unit of newly created fracture surface area.

SPECIFIC EXAMPLES, MAJOR COMPONENTS, AND ALTERNATIVES

The following examples describe selected aspects of exemplary systems and methods for crack growth detection. These examples are intended for illustration and should not be interpreted as limiting the entire scope of the present disclosure. Each example may include one or more distinct inventions, and/or contextual or related information, function, and/or structure.

Example 1

This example describes an illustrative crack propagation detection system 20 and an illustrative test specimen 22; see FIGS. 1-5.

Test specimen 22 may include a single component or may include multiple components. In some examples, test specimen may be a single sheet or plate, which may include a bend or a notch (such as a cutout). In other examples, test specimen 22 may be a composite material having two or more constituent materials with significantly different physical or chemical properties. For example, the constituent materials may include a matrix (or bond) material, such as a resin (e.g., thermoset epoxy) and a reinforcement material, such as a plurality of fibers (e.g., a woven layer of carbon fibers). Test specimen may include a surface 23 (such as a top surface), which may be a color contrasted surface. In some examples, surface 23 may include a color contrasting coating 23'. The color contrast coating may be a film, a paint (such as a spray paint), a stain, a varnish, a lacquer, a glaze, and/or other suitable coating. In some examples, such as when test specimen includes two or more layers, surface 23 may be a color contrasted top layer 23".

Crack propagation detection system 20 may include a test platform 24. Test platform 24 may include any suitable structure configured to support test specimen 22 and/or apply stress load(s) to the test specimen. Test platform 24 may include one or more holder assemblies 26, which may include any suitable structure configured to attach to suitable portion(s) of test specimen 22. The holder assemblies may, for example, include clamps, grips, fixtures, etc. to attach to the test specimen. Test platform 24 may apply stress load(s) through holder assemblies 26 and/or separate from those assemblies. For example, when the test platform performs a fracture toughness test on the test specimen, the holder assemblies may be used to displace the test specimen in opposite directions, as shown in 27. Alternatively, such as when the test platform performs a double cantilevered beam test on test specimen 22, a blade or other structure separate from the holder assemblies may be inserted between and/or through layers of the test specimen. The stress load(s) applied to test specimen 22 may, for example, include tensile, compressive, and/or torsional forces. The test platform may be configured to apply the stress load(s) at any suitable constant or variable rate. For example, test platform 24 may apply stress load(s) via a constant or variable displacement rate, via constant or variable force(s), etc. In some examples, test platform 24 may be in the form of a loading and/or testing chamber.

Figure 2:
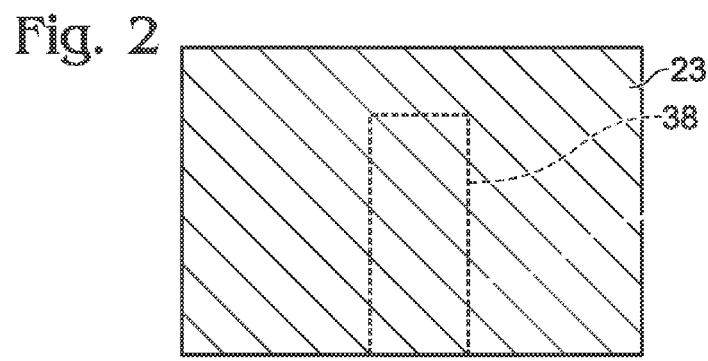
FIG. 2 is a schematic diagram of an illustrative test specimen prior to formation of a crack.
Figure 3:
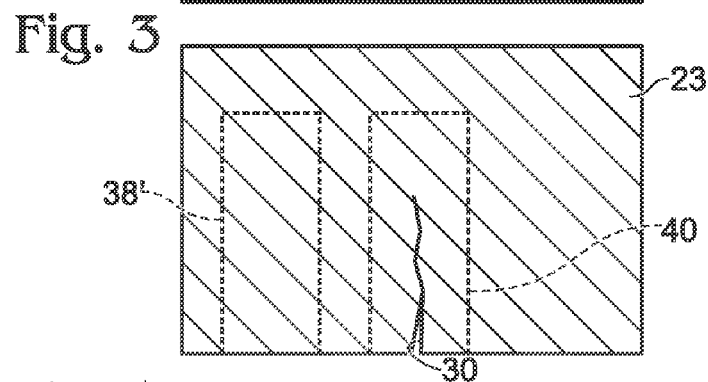
FIG. 3 is a schematic diagram of the test specimen of FIG. 2 during formation and/or propagation of a crack.
Figure 4:
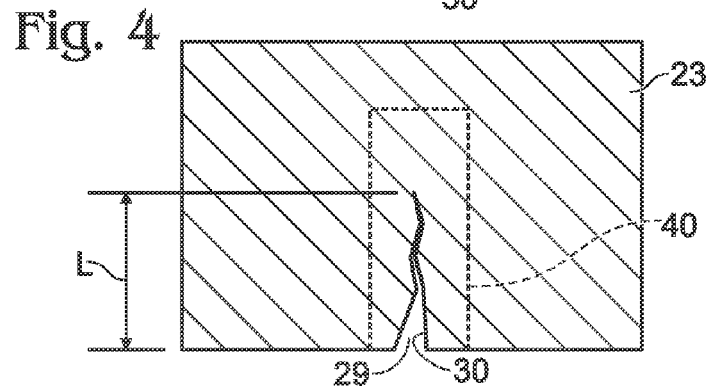
FIG. 4 is a schematic diagram of the test specimen of FIG. 2 during propagation of the crack of FIG. 3.

Test platform 24 also may include a background 28. Background 28 may include a surface (or surface coating) 29. In some examples, the test platform may be configured to support test specimen 22 on or over background 28. For example, test platform 24 may support test specimen 22 such that a camera (discussed below) may capture photographic images of test specimen 22 against background 28. In some examples, surface 23 of test specimen 22 may be color contrasted (or highly contrasted) relative to background 28 (or to surface 29 of that background). For example, as shown in FIGS. 2-4, a test specimen having a light green surface 23 is placed against a background having a white surface 29. The test specimen may be subjected to a constant displacement from the test platform resulting in variable load as shown in FIG. 5 as a crack 30 propagates through the test specimen.

Figure 5:
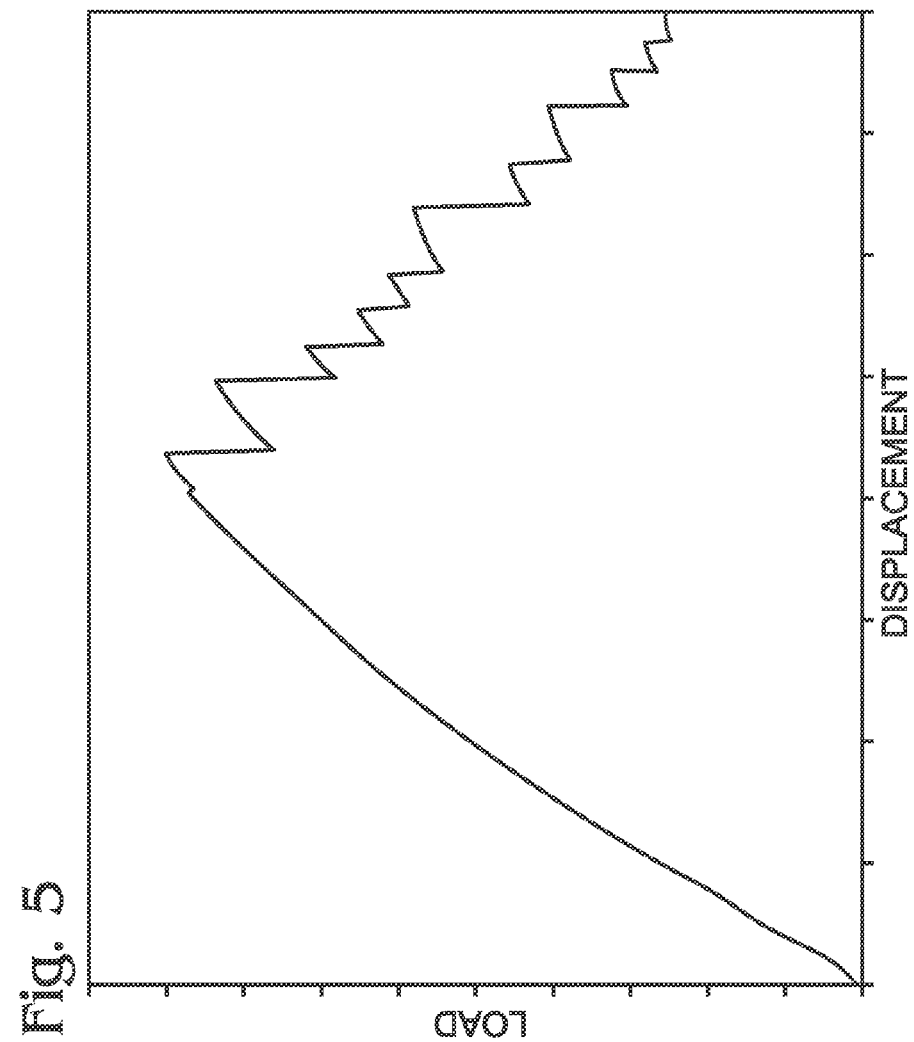
FIG. 5 is an illustrative graph showing load vs. displacement for the stress load applied to the test specimen of FIG. 2.

As shown in FIG. 5, the test specimen may initially exhibit linear elastic behavior. Near a maximum load (or at a critical load), the crack may begin to propagate and increase in size (which may be nearly instantaneously) leading to a drop in the load. As the crack propagates in FIGS. 3-4, the white surface of the background (or sub-material) may be seen through the crack. After the load drops, the test specimen may be able to take on more load again until the crack increases in size once more leading to another drop in the load. The increase and decrease of the load may continue until ultimate failure of the test specimen. Alternatively, a cut or notch may be introduced in the test specimen, such as prior to FIG. 3, resulting in propagation of crack 30 in FIGS. 3-4. Crack 30 has a crack length L in FIG. 4.

Although FIGS. 2-4 show a test specimen having a crack 30 that reveals a portion of the background, the test specimen may have a crack 30 that reveals only the internal component(s) of the test specimen. For example, when test specimen includes multiple layers, crack 30 may reveal only one or more layers (such as one or more inner layers) and not the background. When crack 30 is not expected to reveal the background, the surface 23 may alternatively, or additionally, be color contrasted relative to the color of the interior of the test specimen, such as one or more inner layers of that specimen.

Crack propagation detection system 20 may include a camera 32. The camera may include any suitable structure configured to acquire multiple photographic images of test specimen 22, such as before, during, and/or after application of a stress load to the test specimen. Camera 32 may, for example, be a charge-coupled device (CCD) camera, a complementary metal-oxide semiconductor (CMOS) camera, and/or any suitable camera. The camera may be positioned to acquire photographic images of test specimen 22, such as against background 28.

Crack propagation detection system 20 may include a data processing system, such as a computer 34, having an image processing program 36. The image processing program may receive the photographic images from camera 32 and may be configured to process those images. For example, image processing program 36 may receive photographic images from camera 32 via communication path 37, which may include wireless or wired connections. Additionally, image processing program 36 may be configured to detect pixel characteristics of those images or portion(s) of those received images. In some examples, the image processing program 36 may perform cropping of the images and/or focus on only particular portion(s) of those images.

The image processing program 36 may, for example, be configured to determine pixel characteristics of a representative portion 38 of surface 23 prior to formation of a crack, pixel characteristics of an analysis portion 40 of surface 23 that includes a propagating crack, pixel characteristics of any other suitable portion(s) of test specimen 22, etc. Representative portion 38 may have a color (or at least one pixel characteristic) that is representative of the surface color of the test specimen, while analysis portion 40 may include the area of the test specimen in which crack 30 is expected to form and/or propagate. In some examples, representative portion 38 and analysis portion 40 may be the same portion (as shown in FIGS. 2-4), such as when the image processing program processes one or more photographic images of the test specimen that were taken prior to and during crack formation. In other examples, the representative portion may be a different portion from analysis portion 40 (generally indicated at 38' in FIG. 3), such as when image processing program 36 does not process photographic images of the test specimen that were taken prior to crack formation.

Image processing program 36 may be configured to measure changes in a detected crack length based on detected pixel characteristics, such as pixel characteristics that are outside a baseline range of pixel characteristics and/or that are not associated with the color of surface 23 of test specimen. Image processing program 36 may be configured to generate an output of one or more material characteristics, such as a strain energy release rate, based on propagation of crack length. In some examples, crack propagation system 20 may include a wired or wireless communication path 42 between computer 34 and test platform 24. For example, computer 34 may receive stress load data from the test platform via communication path 42. In some examples, crack propagation system 20 may include a wired or wireless communication path 44 between camera 32 and test platform 24. For example, camera 32 may receive stress load data from test platform 24 and associate that data with the photographic images acquired by the camera. In some examples, camera 32 may communicate with computer 34 such that computer 34 polls test platform 24 for stress load data when camera 32 acquires photographic images.

Example 2

This example describes an image processing program 36 suitable for use with crack propagation detection system 20 as described in Example 1; see FIGS. 6-12.

Image processing program 36 may be configured to determine pixel characteristics of the photographic images, such as pixel intensities, hue, lumosity, and saturation. For example, when the photographic images are black-and-white images, the image processing program may be configured to determine the intensity for each pixel varying from black at the lowest intensity to white at the highest intensity, such as ranging from 0 to 255. When the photographic images are colored images, image processing program 36 may be configured to determine the intensities for each primary color, namely red, green, and blue (RGB). For example, the determined intensities for each primary color may range from 0 to 255 with a 24-bit color scheme.

FIGS. 6-8 show illustrative results of image processing program 36 analyzing pixels 46 and their intensities (or intensity values) 48 for representative portion 38 of test specimen 22 for each primary color (e.g., red 50, green 52, and blue 54). Based on the analysis, the image processing program may determine a baseline range of pixel values, such as a baseline range for each primary color, and/or may determine the pixel values associated with surface 23 of test specimen 22. For example, the baseline pixel intensities for representative portion 38 in FIG. 2 are the following:

Red pixel values that range from 0-12 with an average of 6 and a standard deviation of 2.5;
Green pixel values that range from 150-200 with an average of 175 and a standard deviation of 10; and
Blue pixel values that range from 1-7 with an average of 4 and a standard deviation of 4.

Alternatively, or additionally, the above pixel values are associated with surface 23 of test specimen. The pixel intensities of FIGS. 6-8 represent a light green surface 23 of test specimen 22.

The image processing program also may be configured to determine pixel intensities for each primary color (e.g., red 56, green 58, and blue 60) for analysis portion 40. FIGS. 9-11 show illustrative results of image processing program 36 analyzing pixels 62 and their intensities 64 for analysis portion 40 of test specimen 22 for each primary color. As shown in FIGS. 9-11, the intensities for most pixels for each primary color remained about the same except for 29 pixels of the 240 pixels shown in FIGS. 6-8. In those 29 pixels, the pixel intensities increased to 250-255 for each primary color representing the white background that can be seen because of the crack in the light green surface of the test specimen.

Based on the determined pixel intensities, image processing program 36 may be configured to detect pixel intensities that are outside a baseline range of pixel intensities and/or that are different from the pixel intensities associated with color contrasted surface 23, which may be indicative of a contrast between crack 30 in test specimen 22 and surface 23 of that specimen. In the above example, the image processing program may be configured to detect: (a) pixel intensities among the red pixels that are different from the range of 0-12 of pixel intensities (or that are outside the baseline range of 0-12); (b) pixel intensities among the green pixels that are different from the range of 150-200 of pixel intensities (or that are outside the baseline range of 150-200); and (c) pixel intensities among the blue pixels that are different from the range of 1-7 of pixel intensities (or that are outside the baseline range of 1-7).

In some examples, image processing program 36 may be configured to detect pixel intensities that are outside a baseline range of pixel intensities and/or that are different from the pixel intensities associated with color contrasted surface 23 by at least a preselected margin for one or more of the primary colors. The preselected margin may be any suitable margin. For example, the preselected margin may be a constant intensity value, such as 25, 50, or 100. Alternatively, the preselected margin may be based on the range or standard deviation of pixel intensities for one or more primary colors. The preselected margin may be, for example, at least one half of the difference between highest and lowest pixel intensities. In the above example, the preselected margins may be as follows: red=6, green=25, blue=4. Image processing program 36 may be configured to detect pixel intensities that are at least the highest intensity value of the baseline range plus (or minus) the selected margin. In the above example, the image processing program may be configured to detect red pixel intensities that are 18 or higher (12+6), green pixel intensities that are 225 or higher (200+25) or 125 or lower (150−25), and/or blue pixel intensities that are 11 or higher (7+4).

In some examples, the preselected margin may be based on a highly contrasted surface 23 relative to the background. For example, the preselected margin may be at least three standard deviations for each RGB intensity, respectively, as found in the representative portion of the test specimen.

Figure 12:
FIG. 12 is a schematic diagram of an illustrative matrix generated based on the schematic diagrams of FIGS. 9-11.

FIG. 12 shows an illustrative matrix 66 that may be generated by image processing program 36 based on processing performed in FIGS. 6-11. The matrix may include a plurality of result values 68. In some examples, each result value 68 may represent a pixel 62. The result values may indicate whether the image processing program detected surface 23 or detected crack 30. For example, result values may be a "0" indicating that surface 23 was detected or a "1" indicating that crack 30 was detected. In some examples, image processing program 36 may assign a "0" to a pixel of analysis portion 40 if the intensity of that pixel is within the baseline range of pixel intensities (or is within the baseline range plus a preselected margin of pixel intensities) and/or is the same as the pixel intensities associated with surface 23. In contrast, image processing program 36 may assign a "1" to a pixel of analysis portion 40 if the intensity of that pixel is outside the baseline range of pixel intensities (or is outside the baseline range of pixel intensities by at least a preselected margin) and/or is different from the pixel intensities associated with surface 23.

In some examples, image processing program 36 may calculate crack length L based on the longest column or row of pixels with a result value of "1". The longest column or row of "1"s may include one or more "0"s, particularly if the crack is not linear, as shown in FIG. 4. For example, the image processing program may identify the longest column or row of pixels with a result value of "1," count the number of pixels in that column or row, and then convert the number of pixels into a crack length measurement based on pixels per length conversion. The pixels per length conversion may be based on a characteristic dimension in one or more photographic images. For example, if the photographic image shows only the entire width of the specimen (without showing the background), then the pixels per length conversion is based on the width of the specimen and the number of pixels across that width.

In some examples, image processing program 36 may calculate crack length L for one or more photographic image and may associate a stress load for each calculated crack length. The calculated crack length and associated load may be used by the image processing program to calculate one or more material characteristics, such as a strain energy release rate. For example, the image processing program may calculate strain energy release rate using the equation below.

$$G := [\partial U/\partial A]_P = -[\partial U/\partial A]_u$$

Here, G is the strain energy release rate, U is the elastic energy of the system, A is the crack area (equal to crack length multiplied by thickness), P is the load, and u is displacement. The image processing program may calculate strain energy release rates using other equations, such as the equations provided in ASTM International D 5045-99 (Reapproved 2007): *Standard Test Methods for Plane-Strain Fracture Toughness and Strain Energy Release Rate of Plastic Materials*, June 2007, 9 pages.

Although image processing program 36 is shown to determine crack length based on pixel intensities, the image processing program may additionally, or alternatively, determine crack length based on detecting and comparing hue, lumosity, saturation, and/or other pixel characteristics. For example, the image processing program may determine the hue (or hue value) for each pixel in the representative portion and determine if there are pixels in the analysis portion with hues outside a baseline range and/or are different from hues associated with the representative portion, which may be indicative of a contrast between a crack and the test specimen.

Example 3

This example describes a method for detecting crack propagation in material test specimen; see FIG. 13.

FIG. 13 depicts multiple steps of a method, which may be performed in conjunction with crack propagation system 20 according to aspects of the present disclosure. Although various steps of method 100 are described below and depicted in FIG. 13, the steps need not necessarily all be performed, and in some cases may be performed in a different order than the order shown.

Method 100 may include a step 102 of color contrasting a surface of a test specimen. Color contrasting the surface may include applying a color contrasting coating to the surface of the test specimen, such as spray painting the surface. In some examples, the coating may exhibit a highly contrasting color relative to the surface color of the background. When the test specimen includes two or more layers, color contrasting the surface may include providing a color contrasting top layer. Alternatively, or additionally, color contrasting the surface may include selecting a surface color of a background that color contrasts the surface of the test specimen. When the test specimen is a composite material test specimen, color contrasting may be performed on a surface of that specimen.

Method 100 may include a step 104 of supporting the test specimen over a background (or background area). At step 104, the test specimen may be supported such that the surface color of the background may be visible through a crack in the test specimen.

Method 100 may include a step 106 of applying a stress load to the test specimen. When holder assemblies are used to attach to portions of the test specimen, step 106 may include moving one or more of those holder assemblies apart, together, and/or in torsion to apply the stress load. Alternatively, the holder assemblies may hold the test specimen in place while a stress load from another component of a test platform is applied. The applied stress load may, for example, be a constant or variable force and/or be a constant or variable displacement of the test specimen. At step 108, photographic images of the test specimen may be acquired prior to, during, and/or after application of the stress load.

Method 100 may include a step 110 of processing the photographic images. At step 110, one or more of the photographic images may be processed to determine a baseline range of pixel characteristics and/or pixel characteristics associated with the surface of the test specimen. At step 110, the photographic images may be processed to detect characteristics of pixels that are outside a baseline range of pixel characteristics and/or that are different from pixel characteristics associated with the color of the surface of the test specimen, which may be indicative of a contrast between a crack in the test specimen and the surface of that specimen. In some examples, the photographic images may be processed to detect characteristics of pixels that are outside a baseline range of pixel characteristics by a preselected margin, such as at least one half of the difference between highest and lowest pixel characteristic values or three standard deviations. The pixel characteristics may, for example, include intensity, hue, lumosity, and/or saturation.

Method 100 may include a step 112 of generating output. At step 112, the output may include measured crack length(s) and/or stress load(s) associated with those length(s). Alternatively, or additionally, the output may include a strain energy release rate based on changes of detected crack length over time and/or propagation of the crack length.

Example 4

Figure 14:
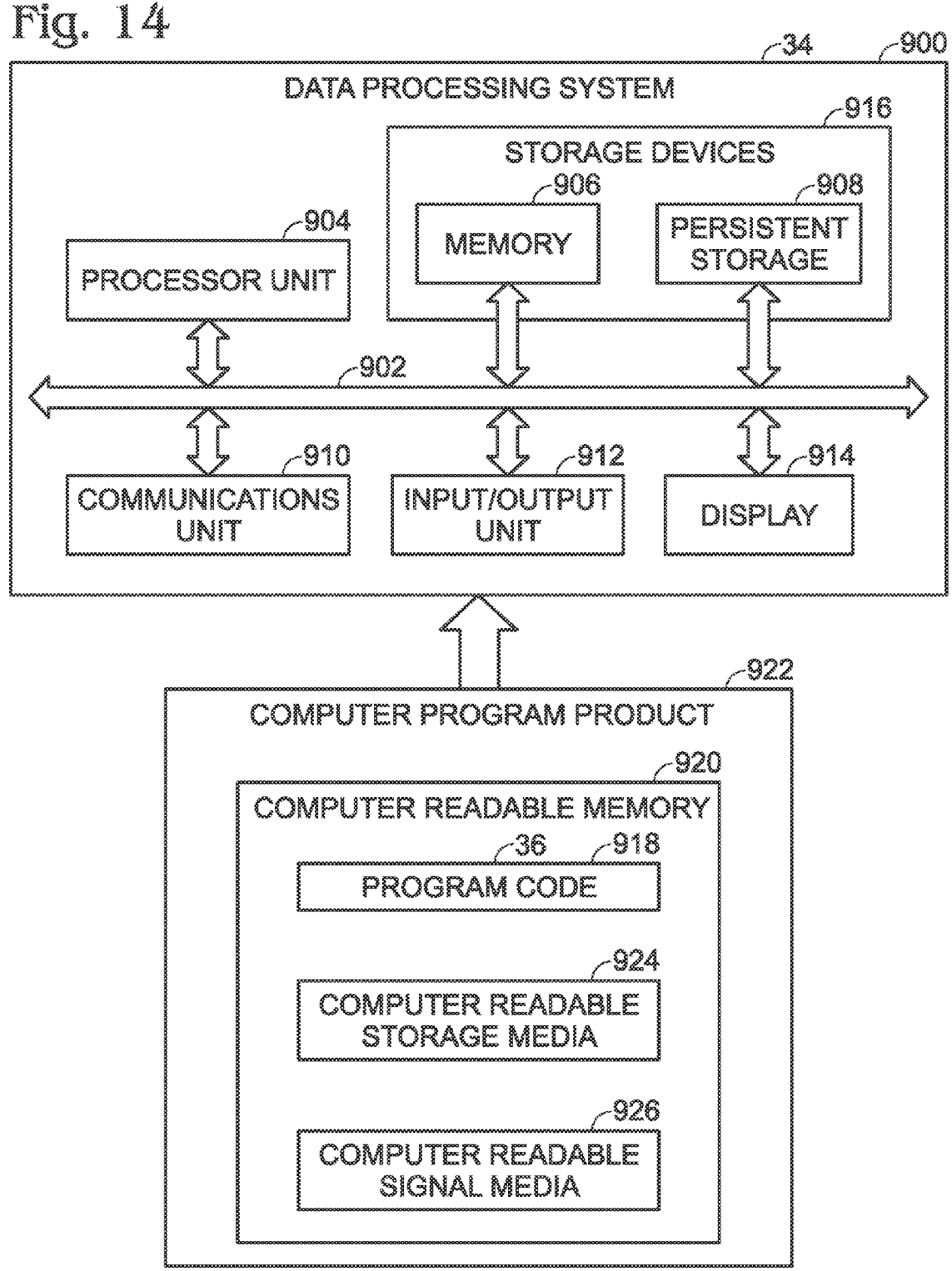
FIG. 14 is a schematic diagram of various components of an illustrative data processing system.

This example describes a data processing system 900 in accordance with aspects of the present disclosure. In this example, data processing system 900 is an illustrative data processing system for implementing computer 34 of crack propagation detection system 20 in FIG. 1; See FIG. 14.

In this illustrative example, data processing system 900 includes communications framework 902. Communications framework 902 provides communications between processor unit 904, memory 906, persistent storage 908, communications unit 910, input/output (I/O) unit 912, and display 914. Memory 906, persistent storage 908, communications unit 910, input/output (I/O) unit 912, and display 914 are examples of resources accessible by processor unit 904 via communications framework 902.

Processor unit 904 serves to run instructions for software that may be loaded into memory 906, such as instructions to process a plurality of photographic images to determine pixel characteristics. Processor unit 904 may be a number of processors, a multi-processor core, or some other type of processor, depending on the particular implementation. Further, processor unit 904 may be implemented using a number of heterogeneous processor systems in which a main processor is present with secondary processors on a single chip. As another illustrative example, processor unit 904 may be a symmetric multi-processor system containing multiple processors of the same type.

Memory 906 and persistent storage 908 are examples of storage devices 916. A storage device is any piece of hardware that is capable of storing information, such as, for example, without limitation, data, program code in functional form, and other suitable information either on a temporary basis or a permanent basis. For example, storage devices 916 may store crack measurement data obtained from the processing of the photographic images.

Storage devices 916 also may be referred to as computer readable storage devices in these examples. Memory 906, in these examples, may be, for example, a random access memory or any other suitable volatile or non-volatile storage device. Persistent storage 908 may take various forms, depending on the particular implementation.

For example, persistent storage 908 may contain one or more components or devices. For example, persistent storage 908 may be a hard drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these examples, provides for communications with other data processing systems or devices. In these examples, communications unit 910 is a network interface card. Communications unit 910 may provide communications through the use of either or both physical and wireless communications links. For example, communications unit 910 may provide for communications with test platform 24 and/or camera 32.

Input/output (I/O) unit 912 allows for input and output of data with other devices that may be connected to data processing system 900. For example, input/output (I/O) unit 912 may provide a connection for user input through a keyboard, a mouse, and/or some other suitable input device. Further, input/output (I/O) unit 912 may send output to a printer. Display 914 provides a mechanism to display information to a user, such as information regarding the measured crack lengths and/or calculated strain energy release rates.

Instructions for the operating system, applications, and/or programs may be located in storage devices 916, which are in communication with processor unit 904 through communications framework 902. In these illustrative examples, the instructions are in a functional form on persistent storage 908. These instructions may be loaded into memory 906 for execution by processor unit 904. The processes of the systems and methods for detecting crack growth may be performed by processor unit 904 using computer-implemented instructions, which may be located in a memory, such as memory 906. The computer-implemented instructions may, for example, include instructions to process photographic images and generate output from that processing.

These instructions are referred to as program instructions, program code, computer usable program code, or computer readable program code that may be read and executed by a processor in processor unit 904. The program code in the different embodiments may be embodied on different physical or computer readable storage media, such as memory 906 or persistent storage 908.

Program code 918, such as image processing program 36, is located in a functional form on computer readable media 920 that is selectively removable and may be loaded onto or transferred to data processing system 900 for execution by processor unit 904. Program code 918 and computer readable media 920 form computer program product 922 in these examples. In one example, computer readable media 920 may be computer readable storage media 924 or computer readable signal media 926.

Computer readable storage media 924 may include, for example, an optical or magnetic disk that is inserted or placed into a drive or other device that is part of persistent storage 908 for transfer onto a storage device, such as a hard drive, that is part of persistent storage 908. Computer readable storage media 924 also may take the form of a persistent storage, such as a hard drive, a thumb drive, or a flash memory, that is connected to data processing system 900. In some instances, computer readable storage media 924 may not be removable from data processing system 900. For example, image processing program 36 may be stored in computer readable storage media that is not removable from computer 34.

In these examples, computer readable storage media 924 is a physical or tangible storage device used to store program code 918 (such as image processing program 36) rather than a medium that propagates or transmits program code 918. Computer readable storage media 924 is also referred to as a computer readable tangible storage device or a computer readable physical storage device. In other words, computer readable storage media 924 is a media that can be touched by a person.

Alternatively, program code 918 may be transferred to data processing system 900 using computer readable signal media 926. Computer readable signal media 926 may be, for example, a propagated data signal containing program code 918. For example, computer readable signal media 926 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 918 (such as image processing program 36) may be downloaded over a network to persistent storage 908 from another device or data processing system through computer readable signal media 926 for use within data processing system 900, such as computer 34. For instance, program code stored in a computer readable storage medium in a server data processing system may be downloaded over a network from the server to data processing system 900. The data processing system providing program code 918 may be a server computer, a client computer, or some other device capable of storing and transmitting program code 918.

The different components illustrated for data processing system 900 are not meant to provide architectural limitations to the manner in which different embodiments of the systems and methods for detecting crack growth may be implemented. The different illustrative embodiments may be implemented in a data processing system including components in addition to and/or in place of those illustrated for data processing system 900. Other components shown in FIG. 14 can be varied from the illustrative examples shown. The different embodiments may be implemented using any hardware device or system capable of running program code, such as image processing program 36. As one example, data processing system 900 may include organic components integrated with inorganic components and/or may be comprised entirely of organic components excluding a human being. For example, a storage device may be comprised of an organic semiconductor.

In another illustrative example, processor unit 904 may take the form of a hardware unit that has circuits that are manufactured or configured for a particular use, such as detecting crack growth. This type of hardware may perform operations without needing program code to be loaded into a memory from a storage device to be configured to perform the operations.

For example, when processor unit 904 takes the form of a hardware unit, processor unit 904 may be a circuit system, an application specific integrated circuit (ASIC), a programmable logic device, or some other suitable type of hardware configured to perform a number of operations, such as processing photographic images and generating output from that processing. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 918 may be omitted, because the processes for the different embodiments are implemented in a hardware unit.

In still another illustrative example, processor unit 904 may be implemented using a combination of processors found in computers and hardware units. Processor unit 904 may have a number of hardware units and a number of processors that are configured to run program code 918, such as image processing program 36. With this depicted example, some of the processes of detecting crack growth may be implemented in the number of hardware units, while other processes of detecting crack growth may be implemented in the number of processors.

In another example, a bus system may be used to implement communications framework 902 and may be comprised of one or more buses, such as a system bus or an input/output bus. Of course, the bus system may be implemented using any suitable type of architecture that provides for a transfer of data between different components or devices attached to the bus system.

Additionally, communications unit 910 may include a number of devices that transmit data, receive data, or both transmit and receive data, such as pixel characteristics data and crack detection data. Communications unit 910 may be, for example, a modem or a network adapter, two network adapters, or some combination thereof. Further, a memory may be, for example, memory 906, or a cache, such as that found in an interface and memory controller hub that may be present in communications framework 902.

The flowcharts and block diagrams described herein illustrate the architecture, functionality, and operation of possible implementations of systems and methods for detecting crack growth according to various illustrative embodiments. In this regard, each block in the flowcharts or block diagrams may represent a module, segment, or portion of code, which comprises one or more executable instructions for implementing the specified logical function or functions. It should also be noted that, in some alternative implementations, the functions noted in a block may occur out of the order noted in the drawings. For example, the functions of two blocks shown in succession may be executed substantially concurrently, or the functions of the blocks may sometimes be executed in the reverse order, depending upon the functionality involved.

Advantages, Features, Benefits

The different embodiments of the systems and methods of detecting crack propagation in a material test specimen described herein provide several advantages over known solutions. For example, the illustrative embodiments of the system and method of detecting crack propagation described herein allow acquiring of crack formation and propagation data at a much higher rate over known solutions. Additionally, and among other benefits, illustrative embodiments of the system and method of detecting crack propagation described herein allow more accurate determination of material characteristics of components and structures. No known system or device can perform these functions, particularly in a materials testing environment. Thus, the illustrative embodiments described herein are particularly useful for determining material characteristics of components and structures, such as to determine whether those components and structures are suitable for a particular use. However, not all embodiments described herein provide the same advantages or the same degree of advantage.

CONCLUSION

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

I claim:

1. A method of detecting crack propagation in a material test specimen, comprising:
   color contrasting a surface of a test specimen with the surface color of a background;
   supporting the test specimen over the background;
   acquiring a plurality of photographic images of the specimen during application of a stress load;
   processing the plurality of images to detect characteristics of pixels that are outside a baseline range of pixel characteristics indicative of a contrast between the background revealed through a crack in the test specimen and the color contrasted surface of the test specimen; and
   generating an output of a strain energy release rate based on changes in detected crack length over time.

2. The method of claim 1, wherein color contrasting a surface of a test specimen includes applying a color contrasting coating to the surface of the test specimen.

3. The method of claim 1, wherein color contrasting a surface of a test specimen includes providing a color contrasting top layer.

4. The method of claim 1, wherein color contrasting a surface of a test specimen includes selecting a surface color of the background that color contrasts the surface of the test specimen.

5. The method of claim 1, further comprising:
   processing at least one image of the plurality of images to determine a baseline range of pixel characteristics.

6. The method of claim 5, wherein processing at least one image of the plurality of images includes processing a portion of the at least one image, the portion being representative of the color of the surface of the test specimen.

7. The method of claim 1, wherein acquiring a plurality of photographic images of the specimen includes acquiring a plurality of photographic images of the specimen during application of a stress load provided by displacing the test specimen at a constant rate.

8. The method of claim 1, further comprising:
   acquiring a plurality of photographic images before applying the stress load.

9. The method of claim 1, wherein processing the plurality of images to detect characteristics of pixels includes processing the plurality of images to detect intensities of pixels.

10. The method of claim 9, wherein processing the plurality of images to detect intensities of pixels includes processing the plurality of images to detect intensities of pixels that are outside a baseline range of pixel intensities by a preselected margin of at least one half of the difference between highest and lowest pixel intensities for at least one primary color.

11. The method of claim 1, wherein color contrasting a surface of a test specimen includes color contrasting a surface of a composite material test specimen.

12. A system for detecting crack propagation in a material test specimen, comprising:
   a test platform configured to support a material test specimen on a background, the background having a surface color selected to provide a color contrast with a top surface color of the test specimen;
   a camera directed toward the test platform and configured to acquire a plurality of photographic images of the test specimen located on the platform during application of a stress load to the test specimen; and
   an image processing program that receives the plurality of photographic images, and that is configured to:
      detect, in the plurality of photographic images, pixel characteristics of the background revealed through a crack in the test specimen, and
      measure changes in a detected crack length based on the detected pixel characteristics.

13. The system of claim 12, wherein the material test specimen has a top surface coating which is highly contrasted relative to the surface coating of the background.

14. The system of claim 12, wherein the image processing program is further configured to generate an output of a strain energy release rate based on propagation of crack length.

15. A method of detecting crack propagation in a material test specimen, comprising:
   selecting a surface color of a background in a test platform;
   supporting a material test specimen over the background, the specimen having a top surface color contrasting the surface color of the background;
   applying a stress load to the specimen;

acquiring multiple photographic images of an extending crack length in the specimen during the applying step; and detecting pixel characteristics of the background revealed through a crack in the specimen that are different from pixel characteristics associated with the top surface color of the specimen to measure crack length in the specimen.

16. The method of claim 15, further comprising:

generating an output of a strain energy release rate based on propagation of the crack length.

17. The method of claim 15, further comprising:

applying a coating on the test specimen exhibiting a highly contrasting color relative to the surface color of the background.

18. The method of claim 15, further comprising:

detecting pixel characteristics of a portion of at least one image of the multiple photographic images, the portion being representative of the top surface color of the test specimen.

19. The method of claim 18, further comprising:

determining pixel characteristics associated with the top surface color from the detected pixel characteristics.

20. The method of claim 15, wherein detecting pixel characteristics includes detecting pixel intensities that are different from pixel intensities associated with the top surface color to measure crack length in the specimen.

* * * * *